United States Patent [19]
Wilson

[11] Patent Number: 5,369,483
[45] Date of Patent: Nov. 29, 1994

[54] ANALYSIS OF POLYMER MELT STREAM

[75] Inventor: Phillip E. Wilson, Asheville, N.C.

[73] Assignee: BASF Corporation, Parsippany, N.J.

[21] Appl. No.: 59,451

[22] Filed: May 7, 1993

[51] Int. Cl.$^5$ ............................. G01J 3/42; G01J 3/50
[52] U.S. Cl. .................................. 356/300; 356/328; 356/410
[58] Field of Search ............... 356/300, 319, 326, 328, 356/402, 409, 410, 411, 432, 436, 440

[56] References Cited

U.S. PATENT DOCUMENTS

| | | | |
|---|---|---|---|
| 3,740,155 | 6/1973 | Keller et al. | 356/409 |
| 4,516,864 | 5/1985 | Kim et al. | |
| 4,529,306 | 7/1985 | Kilham et al. | |
| 4,717,827 | 1/1988 | Harvey | 356/246 |
| 4,888,484 | 12/1989 | Harvey | 356/434 |
| 4,910,403 | 3/1990 | Kilham et al. | |
| 5,062,713 | 11/1991 | Farquharson et al. | |

OTHER PUBLICATIONS

Stephen J. Swarin and Charlene A. Drumm, "Predicting Gasoline Properties Using Near-IR Spectroscopy", *Spectroscopy*, Sep. 1992, pp. 42–49.

*Primary Examiner*—F. L. Evans
*Attorney, Agent, or Firm*—Karen M. Dellerman

[57] ABSTRACT

The concentration of a colorant in a stream of molten polymer is measured by inserting a probe adjacent to the stream. The probe has integral therein collection means and illumination means. The steam is illuminated with the illumination means to cause electromagnetic radiation to be reflected from the molten polymer. The electromagnetic reflectance is collected, transmitted to a measurement device remote from the molten stream and quantified as a function of the concentration of the colorant.

12 Claims, 5 Drawing Sheets

ANALYSIS OF POLYMER MELT STREAM

FIELD OF THE INVENTION

The present invention relates generally to measuring the concentration of additives in a flowing polymer. More particularly, the present invention relates to measuring the concentration of colorant in a molten thermoplastic stream.

BACKGROUND OF THE INVENTION

As used herein, the term "fiber" includes fibers of extreme or indefinite length (filaments) and fibers of short length (staple).

As used herein, the term "solution-dyed" describes an item that has been colored by the introduction of colorants into the polymer melt or spinning solution prior to shaping.

As used herein, the term "colorant" means a coloring agent which is a water-soluble dye, organic-soluble dye, polymer-soluble dye, pigment or any color imparting agent.

Precise measurement and control of the concentration of color in polymer processing is essential for ensuring that the end products, for example, yarn made into fabric or carpet, is the desired color. Consistency in color is important in the manufacture of textiles and carpets to allow color matching of products made from different lots of materials.

Traditionally, the concentration of colorants in a stream of molten polymer has been measured off-line by forming fibers or plaques and then taking measurements from these samples. There are several drawbacks to these off-line procedures. First, the procedure is time-consuming. The concentration of color is adjusted into the appropriate value by trial and error. Color values are not readily available. Also, the time to obtain results is usually hours.

Several in-line methods for measuring various attributes of polymer melt flows have been proposed. These methods, however, also suffer from various drawbacks. For example, U.S. Pat. No. 4,516,864 to Kim et al. ("Kim") teaches the use of infrared radiation directed through a fiber optic cable to effect temperature measurements. These measurements are accomplished by placing windows opposite each other in the flow channel. The use of two windows requires invasion of the flow in two places with diametrically opposing ports.

Another example of melt stream analysis is found in U.S. Pat. No. 4,529,306 to Kilham et al. ("Kilham '306"). Kilham '306 relies on the fact that polymers are virtually transparent when molten and passes a beam of visible light through a flow of the polymer melt to observe the illuminated polymer stream either visually or using a video camera. The system employs fiber optics to transmit the illumination and allow the observation of the illuminated stream. The Kilham '306 invention relates to the detection of impurities and gels within a polymer melt and no quantitative analysis is performed. Furthermore, Kilham '306 requires two points of intrusion into the molten polymer path, one for providing visible light and the other for observing the illuminated flow.

U.S. Pat. No. 4,910,403 to Kilham et al. ("Kilham '403") teaches the use of a specially designed diamond flow cell to effect measurements using near to far infrared energy. The sample cell possesses unique characteristics with regard to temperature and pressure resistance. A beam of energy is passed through the sample so that the method involves two invasion points. The use of this flow cell requires the melt flow equipment to be specially adapted.

U.S. Pat. No. 5,062,713 to Farquharson et al. ("Farquharson") discloses a method for determining the residence time distribution of a polymer extruder. This process is useful in designing extruders for optimum performance. The invention passes energy in the visible region through the polymer melt to determine the relative concentration of a colorant in the melt. The colorant is added as a tracer or marker and used to measure the residence time of the colored portion of the polymer. Only two wavelengths are supplied and measured. One wavelength is used to quantify the colorant and the other is used to identify the background spectrum. As with the others, the Farquharson invention requires two points of invasion into the polymer flow system. One of the points is for providing a light source and diametrically opposed to the light source is a detector for detecting transmitted light energy. Farquharson requires also that an optimum wavelength is pre-selected for use.

Fiber optics have been used inline to measure specified properties in other fields, too. See, for example, Stephen J. Swarin and Charlene A. Drumm, "Predicting Gasoline Properties Using Near-IR Spectroscopy", *Spectroscopy*, Sep. 1992, pp. 42–49.

The present invention provides a number of advantages over the discussed art. First, only one window into the process is needed. Also, visible light is used to characterize the color of the polymer melt. Further, the characterization of the color is accomplished by using a plurality of wavelengths covering the entire visible spectrum, eliminating the need to optimize and preselect a wavelength. Meaningful color measurements are obtained in minutes, not hours.

SUMMARY OF THE INVENTION

The present invention solves the deficiencies described above in a method for measuring the concentration of a colorant in a stream of molten polymer moving axially through a conduit. The methods includes the steps of inserting adjacent to the stream of molten polymer, a probe having integral therein collection means and illumination means; illuminating the molten stream with the illumination means to cause electromagnetic radiation to be reflected from the molten polymer; collecting the electromagnetic reflectance; supplying the collected electromagnetic reflectance to a measurement device remote from the molten stream; and quantifying the collected electromagnetic reflectance as a function of the concentration of the colorant.

Another embodiment of the present invention is an apparatus for measuring the concentration of colorant in a molten polymer traveling through a conduit. The apparatus is inserted between a pump for pumping the molten polymer and a pump block. The apparatus includes a plate provided with an intake port for receiving molten polymer into the pump, a discharge port for discharging polymer from the pump, and a probe port in communication with the discharge port; a probe disposed in the probe port and having integral therein means for transmitting electromagnetic radiation from a source to the molten polymer and means for collecting electromagnetic radiation reflected from the molten polymer; means for measuring the reflectance of the molten polymer; and in optical communication with the collecting means, means for supplying electromagnetic radiation from the collecting means to the measuring means.

A still further embodiment is an apparatus for measuring the concentration of colorant in a flowing matrix. The apparatus includes a fiber optic probe having a hollow core; a fiber optic bundle disposed within the core, said bundle having both transmitting fibers and receiving fibers; a light transmission window in light transmission communication with the bundle and with the matrix; a light source for transmitting light through the bundle to the window; and a light detector for detecting light transmitted from the matrix through the receiving fibers.

It is an object of the present invention to provide a method for measuring the concentration of an additive, especially a colorant, in a polymer stream moving through a conduit.

Related objects and advantages will become apparent after a reading of the following detailed description.

DETAILED DESCRIPTION OF THE PREFERRED EMBODIMENTS

To promote an understanding of the principles of the present invention, descriptions of specific embodiments of the invention follow and specific language describes the same. It will nevertheless be understood that no limitations of the scope of the invention is thereby intended, and that such alterations and further modifications, and such further applications of the principles of the invention as discussed are contemplated as would normally occur to one ordinarily skilled in the art to which the invention pertains.

Figures 1, 2:
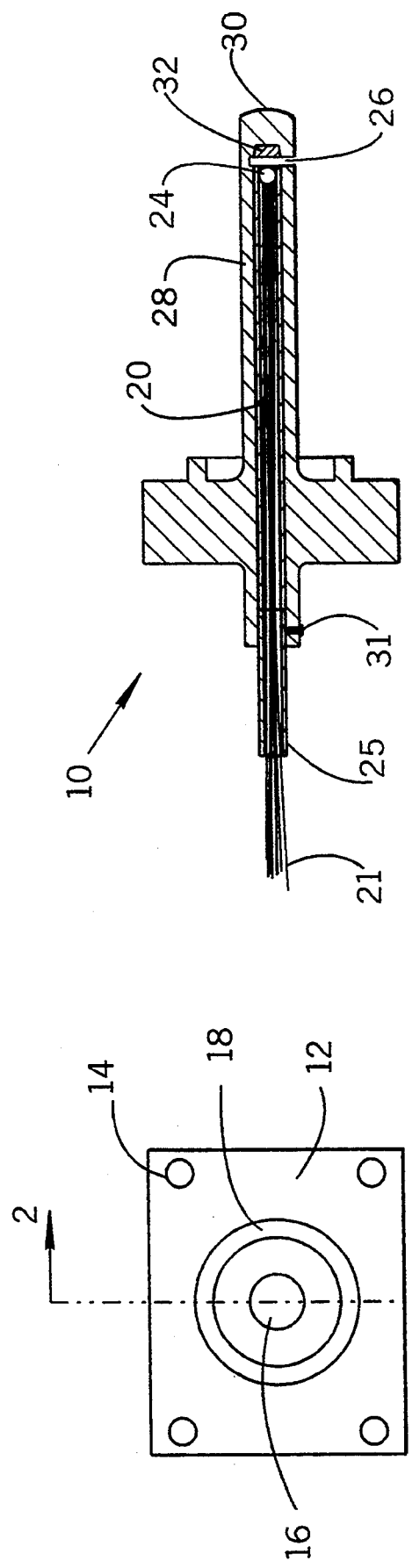
FIG. 1 is a front elevational plan view of a fiber optic color probe useful in the present invention.
FIG. 2 is an elevational cross-sectional view taken along line 2—2 of FIG. 1 and looking in the direction of the arrows.

FIG. 1 is a front elevational plan view of a fiber optic probe assembly 10 useful in the present invention. Probe assembly 10 includes mounting bracket 12 having four through holes 14 for securely attaching probe assembly 10 in a melt stream flow. Through holes 14 receive mounting bolts (not shown). The mounting bolts may be threaded at one end for mating with threaded holes on the melt spinning equipment. For example, the bolts pass through through holes 14 and are attached to threaded parts on the spin pack or conduit. Other means, for example a clamp, may also be used to securely attach the probe assembly to the melt spinning equipment. If a clamp is used, then through holes 14 are not necessary. Regardless of the attaching means used, it is important to make sure that the probe assembly does not cause the melt spinning equipment to leak at the point of entry. Probe 16 itself is shown located approximately in the center of mounting bracket 12 and is surrounded by flange 18 which couples with the conduit conveying the melt stream.

FIG. 2 is an elevational cross-sectional view taken along line 2—2 of FIG. 1 and looking in the direction of the arrows to illustrate the internal parts of probe assembly 10. Probe assembly 10 includes channel 20 for receiving fiber optics 21 in light transmission communication with sapphire window 24. The transmitting optics can be randomly distributed or concentric or segmented with the receiving optics. Notch 26 is cut into probe body 28 near tip 30 to permit molten polymer flow between sapphire window 24 and reflective surface 32. As shown, sapphire window 24 is in the form of a ball located at the distal end of the probe. The probe and optics may be coupled by any conventional coupling means. Fibers optics 21 are shown disposed within sheath 25 and coupled to the end of probe assembly 10 via set screw 31. Any other standard coupling method may be used.

Figure 3A:
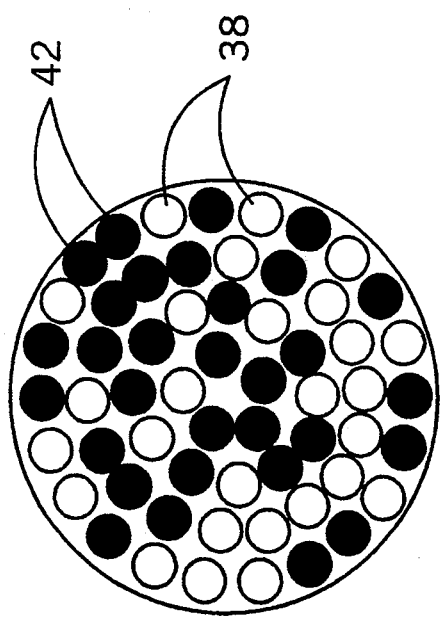
FIGS. 3-3A is a schematic of a probe and detector useful in the present invention.
Figure 3:
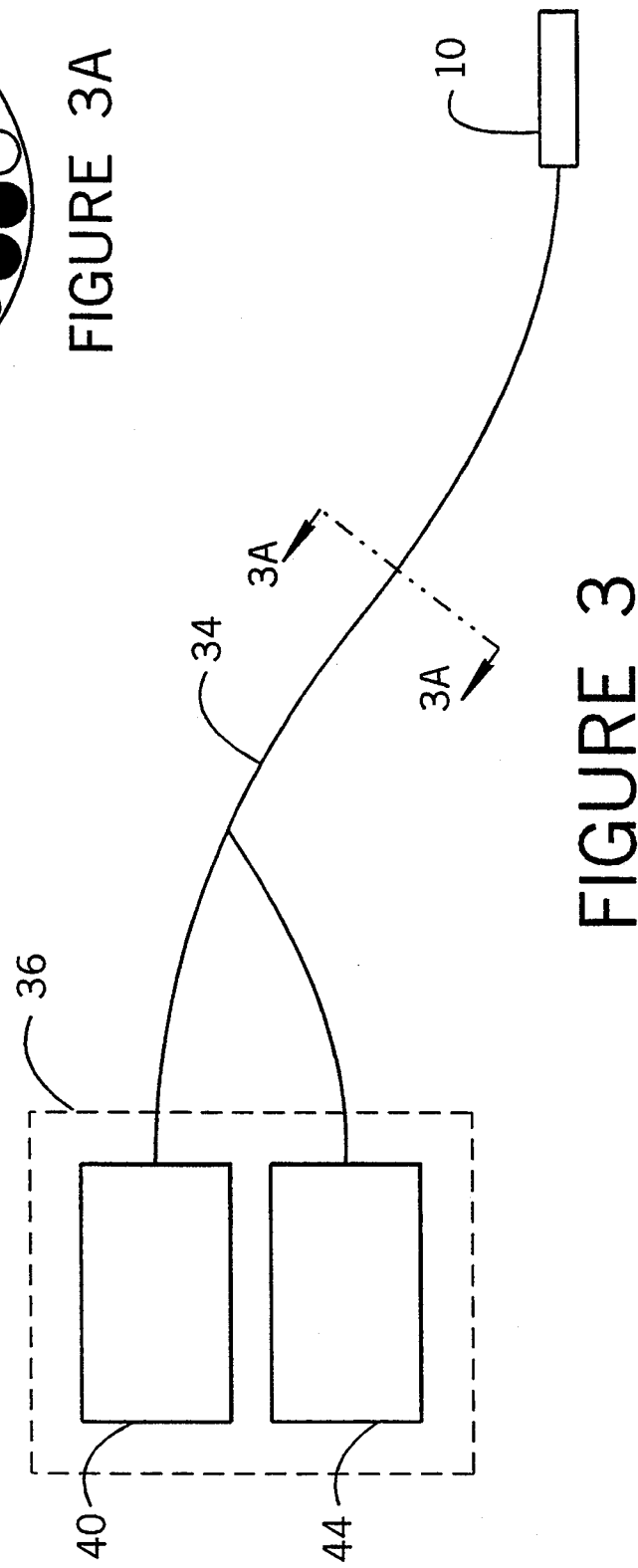

FIG. 3 is a schematic of probe assembly 10 as connected with fiber optic cable 34 and detector 36. Fiber optic cable includes fiber optics 21 and sheath 25.

FIG. 3A is an exploded cross-sectional view of fiber optic cable 34 showing both light transmitting and light receiving optics. Light transmitting fibers 38 transmit light from light source 40 to the sapphire window (see FIG. 1) while fibers 42 receive light from the reflective surface and supply it to detector 44.

Figure 4:
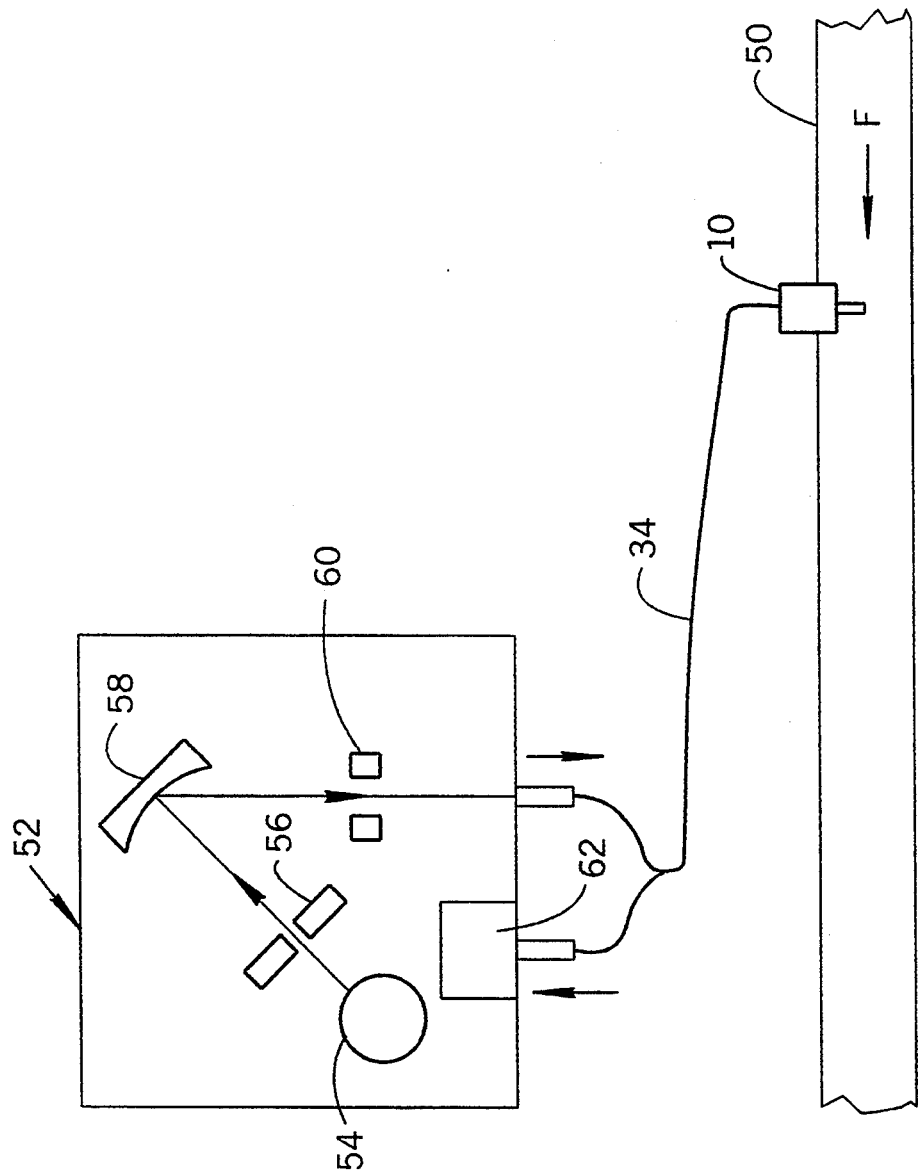
FIG. 4 is a schematic representation of a fiber optic probe installed in a polymer flow according to the present invention.

FIG. 4 is a schematic representation of fiber optic probe assembly 10 inserted into pipe 50. Polymer flows through pipe 50 in the direction of the arrow F. In spectrophotometer 52, light is transmitted from light source 54 through slit 56 to holographic grating 58 and reflected from grating 58 through second slit 60. In this way the band of wavelengths used is adjusted and focused and transmitted via fiber optic cable 34 to probe 10. Light is reflected from the polymer flowing in pipe 50 and returned to the spectrophotometer detector 62 for evaluation of the wavelength of the reflected light.

Figure 5:
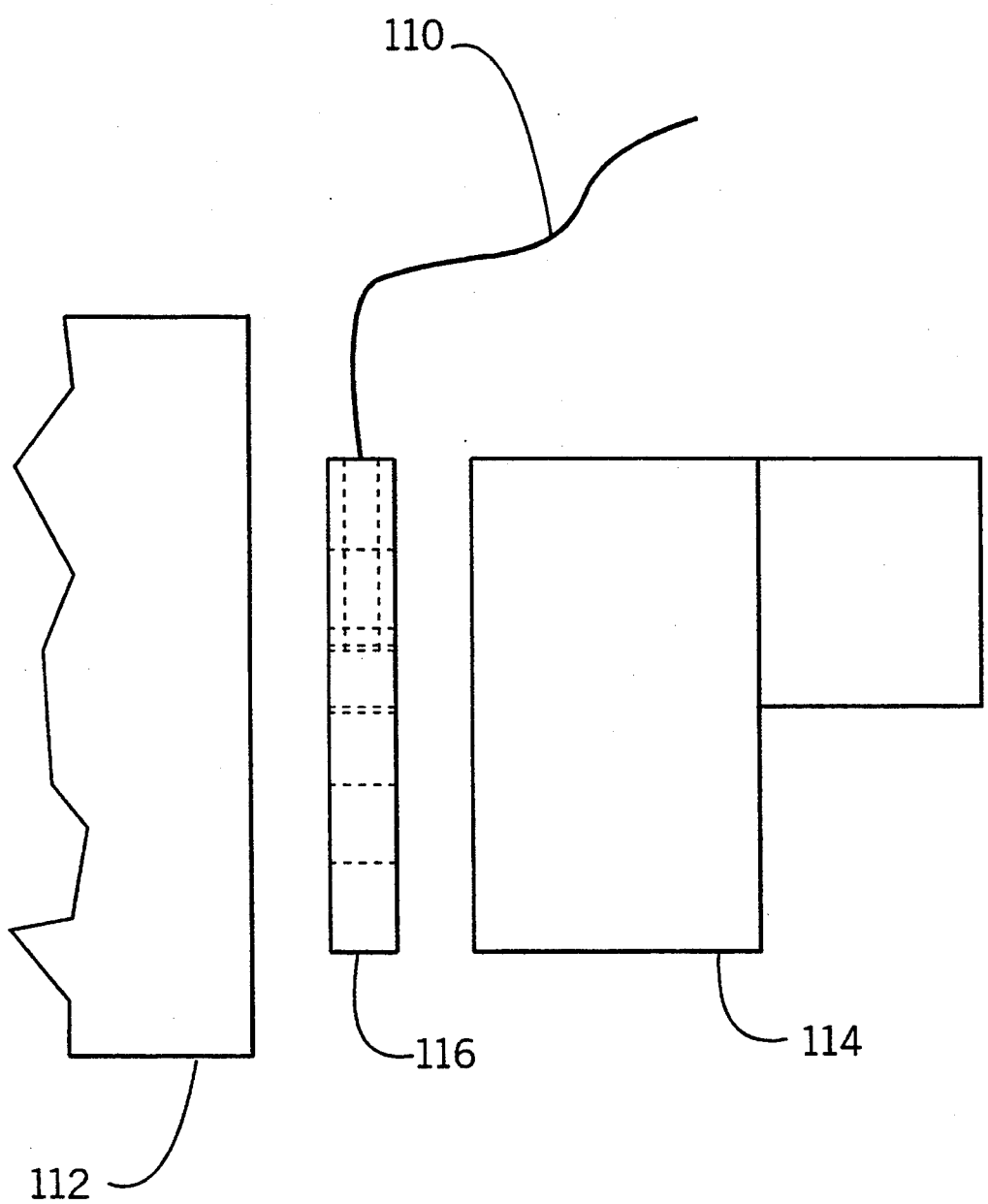
FIG. 5 is an exploded schematic view of an alternate embodiment of the present invention.

FIG. 5 is an exploded schematic view of an alternative embodiment of the present invention wherein fiber optic probe 110 is inserted in a polymer melt processing system between pump block 112 and spin pump 114 via adaptor plate 116 which is adapted for the purpose.

Figure 6:
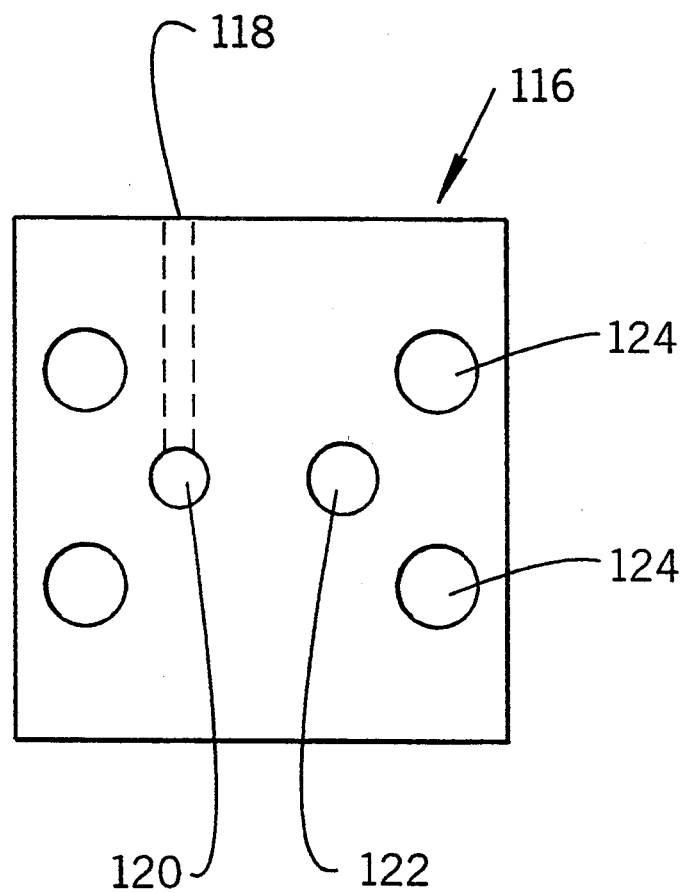
FIG. 6 is an elevational plan view of an adaptor plate suitable for use in the embodiment of FIG. 5.

FIG. 6 shows adaptor plate 116 in elevational plan view. Adaptor plate 116 includes probe port 118 (shown in phantom) which communicates with discharge port 120 which is discharging polymer from the spin pump. Also shown is intake port 122 which takes polymer into the spin pump for discharge. Four through holes 124 are present for receiving bolts which threadingly mate with corresponding holes in the pump block firmly attaching adaptor plate 116 to the pump block.

One manner of coloring fiber forming thermoplastic involves metering colorant to the melt stream. One manner of accomplishing this is using a side-arm extruder, although other apparatus may also be used. By varying the rate of metering, the ratio of colorant to polymer can be expressly determined. This ratio provides the amount of colorant in the spun fiber.

The present invention finds particular use when the intended concentration of colorant in the final product is not readily available. In this case, a target color may be available and the device of the invention is particularly useful for determining when the color of the flowing polymer stream matches the target color. The invention is also useful in verifying that the colorant concentration is indeed within the tolerances of the specified color concentration when the color concentration is known.

In general, the present invention employs the visible light spectrum (about 390 to 770 mm) to determine the colorant concentration and color in a flowing matrix. The selected wavelength range is transmitted through the illuminating (or transmitting) optics to the sapphire window where it illuminates the flowing matrix. A portion of the spectrum is absorbed by the matrix and the rest is reflected from the mirror, collected by the receiving portion of the fiber optics and routed to the detector where a comparison of the sent versus returned light is made. From the intensity and wavelength of the reflected light, the color and colorant concentration of the matrix is quantified.

The invention will be described by referring to the following detailed examples. These examples are set forth by way of illustration and are not intended to be limiting in scope.

EXAMPLE 1

Bright (undelustered) nylon 6 polymer (RV=2.7 as measured in $H_2SO_4$) is spun on a conventional extruder-fed melt spinner. The color concentrate (25 wt. % phthalocyanine blue dispersed in nylon 6) is added via an integral sidearm extruder and first metering device. The nylon 6/color concentrate mixture is subsequently delivered to a second metering device and then to a spinneret pack at a rate of 250 g/min and a temperature of 262° C. After exiting the spinneret, the filaments pass through a cross flow quench chamber 1.9 m in length. Quench air is provided at 15° C. and a cross flow velocity of 150 ft/min. The filaments are then processed on a commercially available drawtexture-interlace-wind machine. The take-up machine is operated at a speed of 2000 m/min.

A probe assembly of the type shown in FIGS. 1 and 2 is introduced into an axially extending walled conduit which conducts polymer between the second metering device and the spinneret. The probe assembly is introduced such that the tip of the device is perpendicular to the direction of travel of the polymer stream. A bidirectional fiber optic bundle is inserted into the probe. As shown in FIG. 3, half of the fibers in the fiber optic bundle propagate electromagnetic radiation from the illumination source (LT Industries Quantum 1200 VIS Analyzer) to the polymer stream. The remaining fibers in the fiber optic bundle receive the electromagnetic radiation reflected from the polymer stream and convey the reflected radiation to a detector in the LT Industries Quantum 1200 VIS Analyzer. The analyzer is configured to operate in the range of wavelengths extending from 400 to 700 nanometers and produce an output which is a function of the intensity of the electromagnetic radiation incident upon the detector. The detector's output is processed to produce a wavelength-dependent transmittance spectrum.

To obtain the transmittance calibration curve, varying known concentrations of colorant are introduced into the polymer stream. With no colorant flowing through the system, a spectrum is taken to serve as a baseline. The first metering device is used to introduce the differing amounts of colorant into the polymer stream. As each amount of colorant is introduced, a spectrum is taken and processed by the system against the baseline. Mathematical relationships are determined which relate the output of the LT Industries Quantum 1200 VIS Analyzer to known levels of colorant. These techniques are applied to determine the level of colorant present in a polymer stream in which the level of colorant is unknown.

The spectral output of the LT Industries Quantum 1200 VIS Analyzer is processed using methods described by the Commission Internationale de l'Eclairage in CIE Publication No. 15 (E-1.3.1) to yield color space coordinates L*, a* and b*.

The results are shown in Table 1 below.

TABLE 1

| True Concentration (%) | Predicted Concentration (%) | L* | a* | b* |
|---|---|---|---|---|
| 0.216 | 0.227 | 4.78 | 1.55 | 6.37 |
| 0.050 | 0.048 | 17.73 | −29.64 | 11.61 |
| 0.100 | 0.099 | 10.40 | −16.91 | 9.47 |
| 0.300 | 0.292 | 3.88 | 4.02 | 5.72 |

What is claimed is:

1. (Amended) A method for measuring the concentration of a colorant in a stream of molten polymer moving axially through a conduit comprising:
   a) inserting adjacent to the stream of molten polymer, a probe having integral therein collection means and illumination means;
   b) illuminating the molten stream with the illumination means to cause electromagnetic radiation to be reflected from and through the molten polymer;
   c) collecting the electromagnetic radiation reflected from and through the molten polymer;
   d) supplying the collected electromagnetic radiation to a measurement device remote from the molten stream; and
   e) quantifying the collected electromagnetic radiation as a function of the concentration of the colorant.

2. The method of claim 1 wherein said illuminating is by providing a predetermined segment of the visible light spectrum from a source to the stream of molten polymer.

3. The method of claim 2 wherein the illuminating means is fiber optics.

4. The method of claim 1 wherein the illuminating means is fiber optics.

5. The method of claim 1 wherein said collecting and said supplying is accomplished with fiber optics.

6. The method of claim 1 wherein said quantifying includes comparing the collected electromagnetic radiation of the melt stream containing colorant to the collected electromagnetic radiation of a melt stream lacking colorant.

7. The method of claim 1 wherein said inserting is by sealingly placing the probe within a conduit which is conveying the molten polymer stream.

8. (Amended) An apparatus for measuring the concentration of colorant in a molten polymer traveling through a conduit, said apparatus inserted between a pump for pumping said molten polymer and a pump block comprising:
   a plate provided with an intake port for receiving molten polymer into said pump, a discharge port for discharging polymer from said pump, and a probe port in communication with said discharge port;
   a probe disposed in said probe port and having integral therein means for transmitting electromagnetic radiation from a source to said molten polymer and means for collecting electromagnetic radiation reflected from and through said molten polymer;

means for measuring the electromagnetic radiation reflected from and through said molten polymer; and in optical communication with said collecting means, means for supplying said collected electromagnetic radiation from said collecting means to said measuring means.

9. The apparatus of claim 8 wherein said transmitting means is a fiber optic bundle disposed in an axial channel of said probe.

10. The apparatus of claim 9 wherein said supplying means is a fiber optic bundle disposed in said axial channel.

11. The apparatus of claim 8 wherein said collecting means is a mirror and a sapphire ball, said mirror and said ball separated by a gap, said gap having molten polymer flowing therethrough, said ball disposed at an end of said transmitting means which is distal to said source.

12. The apparatus of claim 8 wherein said measuring means is a spectrophotometer.

* * * * *

UNITED STATES PATENT AND TRADEMARK OFFICE
CERTIFICATE OF CORRECTION

PATENT NO. : 5,369,483
DATED : November 29, 1994
INVENTOR(S) : Phillip E. Wilson It is certified that error appears in the above-identified patent and that said Letters Patent is hereby corrected as shown below:

At column 6, line 22, please delete "(Amended)" after "1." and before "A".

At column 6, line 56, please delete "(Amended)" after "8." and before "An".

Signed and Sealed this

Fifth Day of January, 1999

Attest:

Attesting Officer

Acting Commissioner of Patents and Trademarks